United States Patent [19]

Whitford

[11] Patent Number: 4,845,978
[45] Date of Patent: Jul. 11, 1989

[54] DETERMINING MOISTURE CONTENT OF A MEDIUM

[76] Inventor: Darryl R. Whitford, Rosedale, Australia, 5350

[21] Appl. No.: 163,369

[22] Filed: Mar. 2, 1988

[30] Foreign Application Priority Data

Mar. 3, 1987 [AU] Australia .................... PI0644

[51] Int. Cl.⁴ ............................. G01N 25/56
[52] U.S. Cl. ............................. 73/73; 73/75; 374/45
[58] Field of Search .......... 73/73, 75, 77; 374/29, 374/44, 45, 54, 136, 137, 155

[56] References Cited

U.S. PATENT DOCUMENTS

| | | | |
|---|---|---|---|
| 2,718,141 | 9/1955 | Richards | 73/75 |
| 2,793,527 | 5/1957 | Turner, Jr. et al. | 73/73 |
| 3,435,400 | 3/1969 | Beckman | 374/155 |
| 3,477,282 | 11/1969 | Ohlheiser | 73/76 |
| 3,491,595 | 1/1970 | Griffeth | 374/155 |
| 3,981,175 | 9/1976 | Hammond, III et al. | 374/10 |
| 4,718,774 | 1/1988 | Slough | 374/7 |

OTHER PUBLICATIONS

Sweat et al., "Automation of a Minature Thermal Conductivity Probe", Conference: Advance in Thermal Conductivity, Lake Ozark, Mo., U.S.A. Nov. 5-7, 1974.

Primary Examiner—William A. Cuchlinski, Jr.
Assistant Examiner—W. Morris Worth
Attorney, Agent, or Firm—Rodman & Rodman

[57] ABSTRACT

A probe for determining moisture content of a medium includes a heating element and a temperature sensing element which is spaced from the heating element. The heating element within a tube is energized for a period of time, and the temperature change of the sensing element after that time is a function of moisture content within a range of tolerance which is acceptable for agricultural and most other purposes. Temperature readout means are coupled to the probe to identify the temperature at that time and identify moisture content of the medium as a function of temperature.

8 Claims, 4 Drawing Sheets

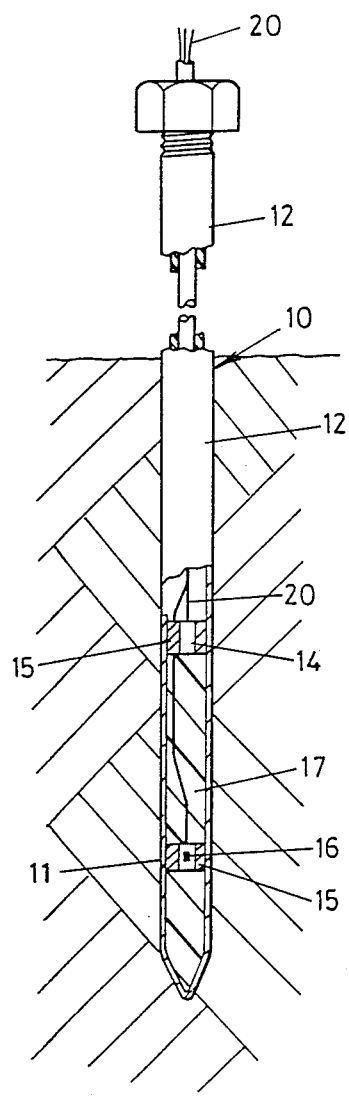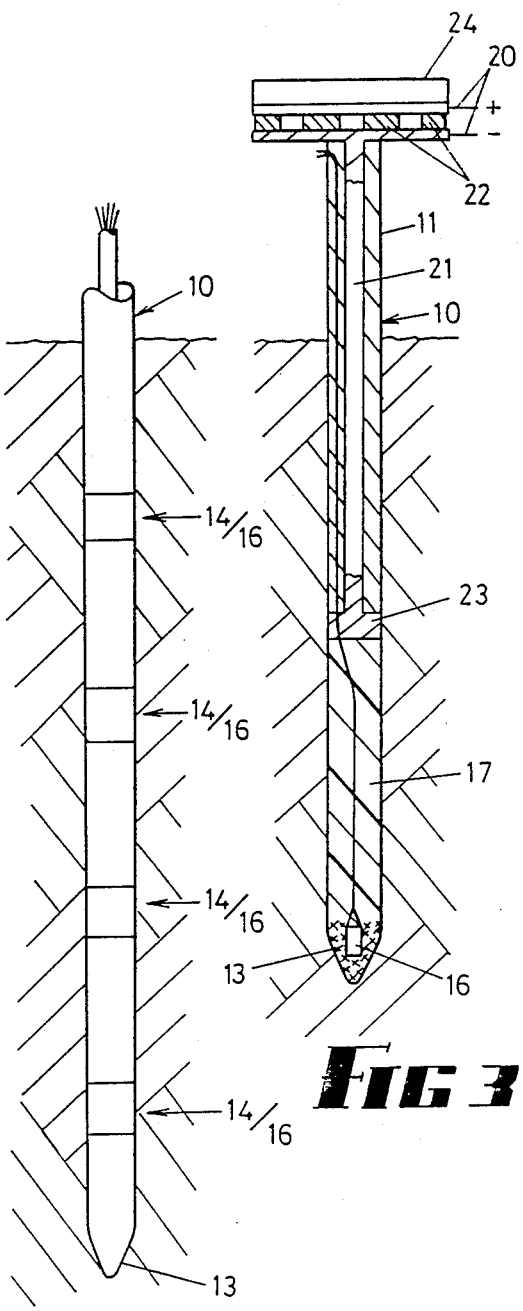

BASIC CIRCUIT CONFIGURATION

CIRCUIT FOR SIMPLE MANUAL READ SYSTEM

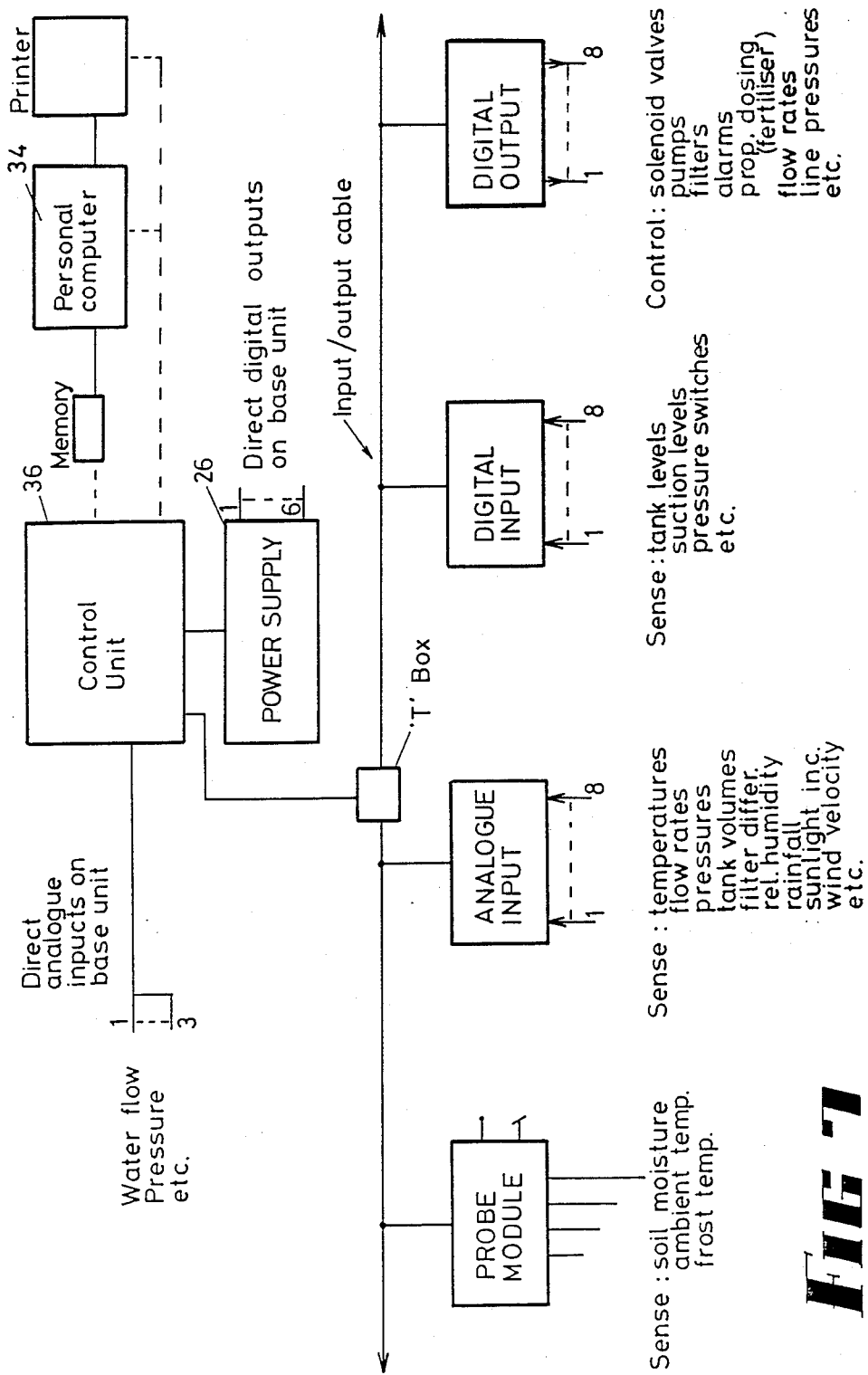

DETERMINING MOISTURE CONTENT OF A MEDIUM

This invention relates to a method for determining the moisture content of a medium, such as soils, and in particular to the construction of a probe suitable for the determination of moisture content of a medium.

BACKGROUND OF THE INVENTION

There are many examples where it is necessary to know accurately the moisture content in a medium. This is particularly relevant in relation to soils where the moisture content is important for agricultural purposes. The ability to determine accurately the moisture content in soils will enable determination of watering rates, and when such watering is required, and is also useful in relation to automatic control of various irrigation systems.

One well known method of determining moisture content of mediums such as soils is the use of electrical conductivity probes. However the sensitivity of such conductivity probes varies greatly with the amount of moisture present, and such probes do not accurately sense moisture content in soils when containing only a small degree of moisture. Also, reading variation is sensitive to the (dry) resistivity of the medium being measured, and variations in the degree of dissolved salts. Other conductivity methods, such as using a porous material in the soil to absorb an equilibrium of moisture suffer from similar problems, and are prone to clogging from fine particulate matter, or sediment from dissolved salts etcetera. Further, it is difficult to use conductivity probes or the like to continuously monitor moisture on a regular, unattached basis, due to variations in reading due to dissolved salts or contamination of the porous material other methods of measuring soil moisture, such as the neutron probe (atomic bombardment of the hydrogen atom), or tension meters (water surface tension suction), by their nature of cost are regulated to the manual measurement, laboratory instrument' class.

Therefore, it is an object of this invention to provide a simple means in determining moisture content in a medium, wherein that means will provide more accurate readings over a wide range of moisture content and soil type, than one available from conductivity probes, while enabling "continuous" regular readings to be obtained automatically, without degradation of the measurement probe.

Soil varies greatly in composition, and can for example comprise coral sand (coralite, comprising absorptive calcium carbonate particles), silicon sand (comprising non-absorptive grains of silicon di-oxide), ironstone particles or pebbles (which are conductive of electricity and heat), as well as the more common clays and loams. A series of tests has shown that utilisation of the specific heat value of the amount of moisture content provides a very much more accurate and sensitive basis for estimating moisture content than previously used variation of electrical conductivity, probably due largely to negligible effect of variation in specific heat due to variation of salt content of water, compared to the very wide differences in electrical resistivity of the soil components.

BRIEF SUMMARY OF THE INVENTION

In this invention a probe for determining moisture content of a medium comprises a heating element and a temperature sensing element which is spaced from the heating element. The heating element is energised for a period of time, and the temperature of the sensing element after that time is a function of moisture content within a range of tolerance which is acceptable for agricultural and most other purposes. Temperature readout means are coupled to the probe to identify the temperature at that time.

Upon inserting the probe into a medium, such as soil, the thermal energy from the heating element is conducted along the heat conduction path of the probe towards the temperature sensing element. Since the heat conduction path is also in contact with the medium, heat will also be transferred to the surrounding area. Although the medium will conduct a given amount of heat away from the probe when in a totally dry condition, the amount to heat conducted by the medium when moist will increase, and will increase at a rate which is a function of the moisture content. Therefore, by measuring the temperature change occurring at the temperature sensing element, over a set period of time, the amount of water present in the medium can be estimated with a degree of accuracy not previously available.

The object of providing a conduction path between the heater and the sensor is to achieve a high degree of sensitivity due to the amount of moisture present. The conduction path effectively provides a high degree of coupling between the thermal energy in the probe to the surrounding soil due to the surface area exposed to and in contact with the soil. An ideal relationship exists where half the energy is lost to the soil (and moisture) when the soil is at a "mid-range" desired moisture content.

It follows then, that the probe can be made particularly responsive for various applications (for example, fibrous potting soil) by adjusting the distance between the heater and the sensor, the thermal conductivity of the probe material and the surface area exposed.

It is useful if the heating element has a constant heat output, such that the only change in heat detected by the sensing element results in heat loss to the surrounding medium. Also, it is important that there is sufficient spatial relationship between the heating element and the temperature sensing element that a reasonable sample of the medium can be measured.

The means for monitoring the output of the temperature sensing element normally monitors a difference in temperature over a period of time, that is, a rate of change of temperature.

BRIEF DESCRIPTION OF THE DRAWINGS

An embodiment of the invention is described hereunder in some detail with reference to, and is illustrated in, the accompanying drawings, in which:

FIG. 1 shows a diagrammatic representation of a probe inserted into soil,

FIG. 2 is a view of a probe having a plurality of heating elements and temperature sensing elements, FIG. 3 shows a probe with the heating element external, FIG. 7 is a block diagram which illustrates a typical agricultural installation wherein use is made of the probes of this invention for determining said moisture content.

DETAILED DESCRIPTION OF THE PREFERRED EMBODIMENT

Figure 4:
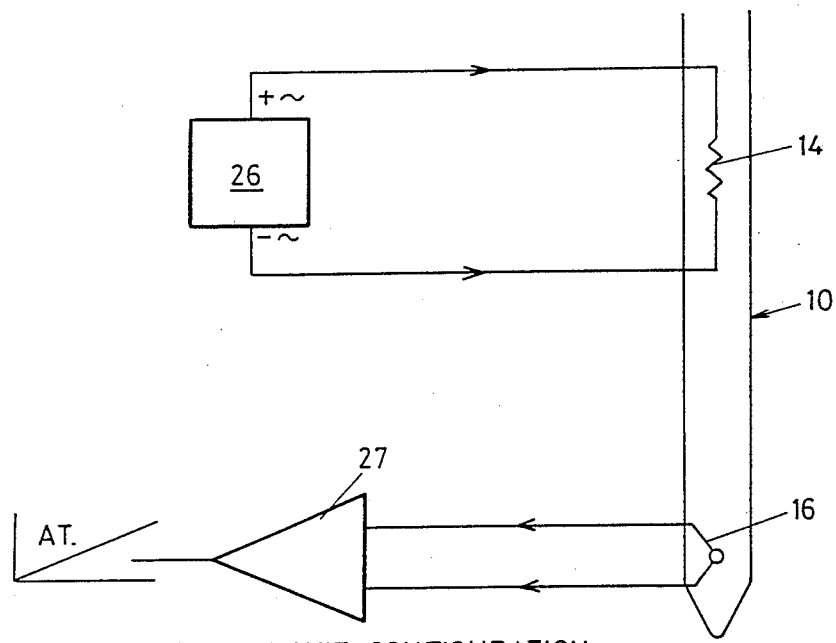
FIG. 4 shows a basic circuit configuration for both the heating element and temperature sensing element.

In this embodiment, the medium in which the moisture content is being measured is soil. However, it will be well understood by persons skilled in the art that the probe in accordance with this embodiment will find application in other physical matter that contains water.

Referring to FIGS. 1, 2 and 3, a probe 10 comprises a stainless steel tube 11 joined to a plastic rod 12 of the same diameter. The tube 11 has a closed and pointed lower end 13 that is designed to be inserted into the soil to the depth required. The preferred method of inserting the probe member is via a pre-drilled hole giving an interference fit with the probe member. Within the upper part of the tube 11 in FIG. 1, there is located an electric heater element 14 which comprises either a resistance heater or a constant voltage zener diode. The heater 14 is thermally bonded by a heat conductive sleeve 15 to the inner wall of the tube 11. At the base of the probe a temperature sensor 16 is also thermally bonded to the inner wall of the tube 11 also by a heat conductive sleeve, and the cavity between the heater element and the temperature sensing element is filled with either a silicon grease or epoxy resin at 17.

The heater element 14 within the probe is energised through conductors 20 so as to provide a constant heat output. This is achieved by either using a fixed resistance and constant voltage source, but a fixed zener diode can be used as the heater element, if provided with a constant current source.

The constant thermal energy from the heater element 14 is conducted through the wall of the tube 11 towards the thermal sensor. As the wall 11 of the probe member is in close contact with the soil, under dry conditions some heat loss will result to the soil particles, and air cavities within the soil. However, in general it is found that soil is not a good thermal conductor, and has a relatively low specific heat and therefore does not conduct a great deal of heat from the probe. However, since water has a high specific heat capacity of 1.0, water present in the soil causes a heat flow from the probe which is a function of the amount of water present. This results in a diminished amount of heat being conducted to the temperature sensing element. Therefore, by measuring the temperature change of the temperature sensor 16 over a set period of time, that is, the rate of temperature change, the amount of water present in the soil can be accurately estimated. Water, not being a good thermal conductor (it is a poor conductor) does not conduct a large degree of heat from the probe due to thermal dissipation. The variation in thermal loss is due to heating the immediate surrounding soil and water present. This lack of conduction results in a reasonably linear relationship between the degree of moisture present and the thermal loss due to raising the mass of moisture in temperature, since otherwise increasing amounts of moisture present would cause more heat to be lost due to thermal conduction as percentage increased, causing a non-linear relationship to occur.

As shown in FIG. 2, by utilizing a multiple probe with several probe heater/sensor combination at various depths, it is possible to establish the moisture profile through a section of soil.

In some instances it is desirable to have the heaters accessible, and in FIG. 3 the probe 10 contains a central heat conductive rod 21 within the stainless steel tube 11 (the rod 21 for example being of copper), and this transfers heat from heater elements 22 to a boss 23. A heat sink 24 radiates heat to the air, but in other respects the probe functions as in FIG. 1, the boss 23 substituting for the heater element 14.

Referring to FIG. 4, the basic circuitry consists of a constant voltage power supply device to the heating element. The temperature sensor 16 comprises a semiconductor sensing unit and the signal from the semiconductor sensing unit is amplified by amplifier 27 to readout means which identifies rise in temperature.

Figure 5:
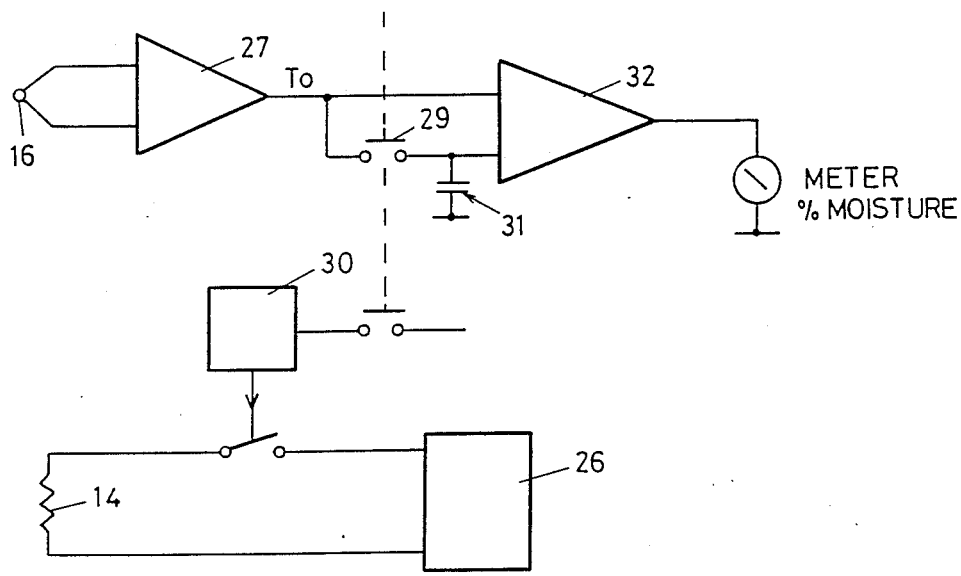
FIG. 5 shows an output control for the circuit of FIG. 4.

FIG. 5 shows a control arrangement for the operation of the electrical circuitry. A manual push button switch 29 is used to activate a timer 30 which in turn connects the power supply 26 to the heater 14 for a given period of time and off at the expiry of that period. The manual push button switch 29 also maintains the voltage drop across the capacitor 31 at the level just prior to activating the push button. This therefore provides the reference input to a differential amplifier 32. At the end of the timer period provided by the timer 30, the amplified difference in temperature will be directly proportional to the moisture percentage within the soil.

Figure 6:
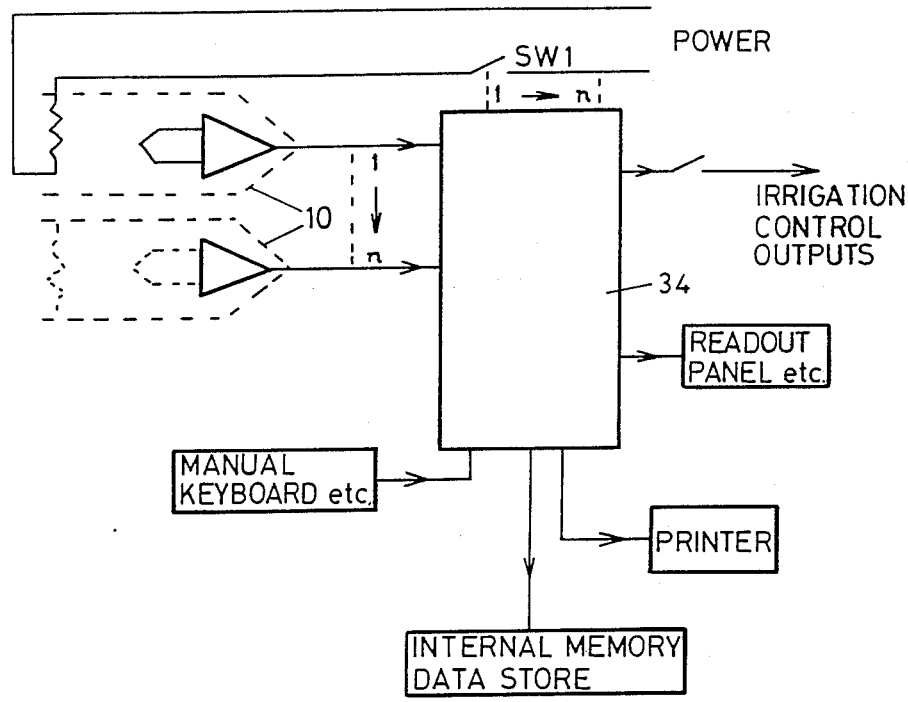
FIG. 6 shows a circuit incorporating a computer as a central processor unit for automatic probe control and moisture level recording.

FIG. 6 shows the use of a microprocessor 34 to control the operation of a plurality of probes 10. The microprocessor controls the switching of each of the probes and is provided with an analogue to digital conversion circuit, arranged so that the analogue signal from each of the probes is converted to digital. The microprocessor 34 is provided with a data memory store, and programmed to provide a print-out of records, or to control various automatic watering devices for irrigation purposes. By using an internal timing clock the microprocessor 34 can at regular intervals switch on the probes 10 and measure the temperature changes from each of the probes. It is preferable that the probes be switched on together so that an accurate indication of soil conditions at that time be obtained. If the probes were to be switched sequentially, soil variations due to variation in time is taken into account by the computer. This circuit, indicating the wide range of parameters which can be processed by the control unit (generally designated 36).

If a computer 34 is used as in FIG. 6 or FIG. 7, there is an additional advantage that compensation can be made for ambient rise or fall in temperature, thereby providing means for further improving accuracy. As illustrated diagrammatically in FIG. 8, two temperature readings may be taken ten minutes apart to determine what temperature change is occurring at the locality of a temperature sensor 16. The temperature difference, $T_1 - T_2$ will be horizontal, will have a negative slope, or will have a positive slope as shown.

After the ambient conditions have been established, the probe heater 14 is energised for a period of 15 minutes. Due to what can be termed "thermal inertia", both of the probe and surrounding soil, a time delay occurs before the consequential change in temperature commences, and the measurement of change in temperature does not commence until the sensor has increased its temperature by 0.1° C. Change of temperature is then measured over the remainder of the 15 minute cycle (minutes).

Figure 8:
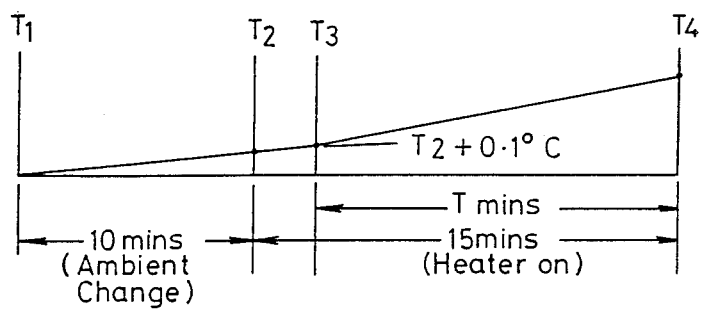
FIG. 8 shows a temperature/time graph wherein ambient change in soil temperature is taken into account.

The increase in temperature, that is, the T value due to soil moisture and soil thermal characteristics, is $$(T4-T3)-(T2-T1)° C.$$

where T1, 2, 3, 4 are the measured temperature at the period in time shown in FIG. 8.

It will be observed that the probes described in the above embodiment require to be switched off for a reasonable time so as to allow the soil around the probe member to return to normal temperature (even though the probe heating cycle only causes the probe and surrounding soil to be raised a few degrees Celsius) before a further reading can be taken. In the embodiment shown in FIG. 3, the heater elements 22 can comprise solid state thermo-electric modules. Theses modules are arranged such that a DC current in one direction will cause heating, and by reversing the DC current a cooling effect can be achieved. By using such a module, regular current reversals will cause the probe to both heat and then cool thereby resulting in a rapid return to normal soil condition. Therefore, using repetitive cycles of DC current flow, more measurements at a quicker rate can be made. If required, the decreasing temperature change can be used to establish moisture content of the soil.

I claim:

1. A probe for determining the moisture content of a particulate medium,
   comprising a tube insertable into said medium and having a wall and an electrical heating element within the tube in a heat conductivity relationship with an outer surface of the tube through the wall,
   a temperature sensing element also within the tube but spaced along the tube from the heating element, and in a heat conductivity relationship with said heating element and said outer surface through the wall,
   conductors connecting the heating element to a supply of electrical energy, timing means coupled to the conductors arranged to initiate passage of energy to said heating element and thereafter terminate passage of said energy after a period of time,
   and moisture readout means coupled to the temperature sensing element so as to determine extent of change in temperature sensed by said temperature sensing element over said period of time,
   and relate moisture content of the medium as a function of said change in temperature.

2. A probe according to claim 1 wherein said tube is a stainless steel tube and contains one of said elements intermediate its ends, and the other said element at one end.

3. A probe according to claim 1, wherein said tube is a stainless steel tube having two ends and an inner surface, one of said ends containing said temperature sensing element, and a heat conductive rod projecting from the other said end, said heating element being carried at the other said end, and a boss on the heat conductive rod engaging the inner surface of the tube at a location spaced from the temperature sensing element.

4. A probe according to claim 1, wherein said supply of electrical energy comprises a constant voltage power supply device.

5. A probe according to claim 4, wherein said temperature sensing element comprises a semi-conductor device, and further comprising an amplifier and means connecting the sensing element to the amplifier.

6. A probe according to claim 4, wherein said timing means comprises a timer operable to connect the power supply device to said heating element, and operable to switch the heating element on for a period of time and off at the expiry of that period.

7. A method of determining moisture content of a particulate medium, comprising inserting into the medium a probe which comprises,
   a tube having a wall, an electrical heating element within the tube in a heat conductivity relationship with an outer surface of the tube through the wall,
   a temperature sensing element also within the tube but spaced along the tube from the heating element, and in a heating conductivity relationship with said heating element and said outer surface through the wall,
   conductors connecting the heating element to a supply of electrical energy, timing means coupled to the conductors arranged to initiate passage of energy to said heating element and thereafter passage of said energy after a period of time,
   and moisture readout means coupled to the temperature sensing element as to determine extent of change in temperature sensed by said temperature sensing element over said period of time and relate said temperature change to moisture content,
   applying electrical energy to the heating element for said period of time, determining the temperature change of the temperature sensing element at the expiry of that period of time, and relating moisture content as a function of that temperature change.

8. A method according to claim 7, further comprising determining the temperature of the temperature sensing element on two occasions which are sufficiently spaced in time to ascertain any ambient temperature change occurring at the locality of the temperature sensing element, determining the temperature change of the temperature sensing element at the expiry of that period of time, forming a compensated temperature change using said temperature change and said ambient temperature change, and relating moisture content as a function of the compensated temperature change.

* * * * *

UNITED STATES PATENT AND TRADEMARK OFFICE
CERTIFICATE OF CORRECTION

PATENT NO. : 4,845,978

DATED : July 11, 1989

INVENTOR(S) : Darryl R. Whitford

Page 1 of 2

It is certified that error appears in the above-identified patent and that said Letters Patent is hereby corrected as shown below:

At column 1,
    line 39, change "tension meters" to --tensiometers--.
    line 41, before "laboratory" insert --'--.

At column 2,
    line 17, change "to" to --of--.

At column 4,
    line 2, change "combination" to --combinations--.

At column 5,
    line 33, before "and" insert --,--.

At column 6,
    line 33, after "thereafter" insert --terminate--.
    line 50, after "element," delete rest of line.
    line 51, delete entire line.

UNITED STATES PATENT AND TRADEMARK OFFICE
CERTIFICATE OF CORRECTION

PATENT NO. : 4,845,978

DATED : July 11, 1989

INVENTOR(S) : Darryl R. Whitford

It is certified that error appears in the above-identified patent and that said Letters Patent is hereby corrected as shown below:

line 52, delete "of time,".

Signed and Sealed this

Twenty-fourth Day of April, 1990

Attest:

HARRY F. MANBECK, JR.

*Attesting Officer*  *Commissioner of Patents and Trademarks*